United States Patent [19]

Lok et al.

[11] Patent Number: 5,912,112
[45] Date of Patent: Jun. 15, 1999

[54] AU(I) SENSITIZERS FOR SILVER HALIDE EMULSIONS

[75] Inventors: Roger Lok, Rochester; Weimar W. White, Canaseraga; Melanie W. Marshall, Webster, all of N.Y.

[73] Assignee: Eastman Kodak Company, Rochester, N.Y.

[21] Appl. No.: 09/035,721

[22] Filed: Mar. 5, 1998

[51] Int. Cl.$^6$ ................................ G03C 1/09; C07F 1/12
[52] U.S. Cl. ..................... 430/603; 430/605; 430/567; 430/569; 556/113
[58] Field of Search ................................ 430/567, 569, 430/603, 605; 556/113

[56] References Cited

U.S. PATENT DOCUMENTS

| | | | |
|---|---|---|---|
| 3,503,749 | 3/1970 | Tavernier et al. | 430/603 |
| 5,049,484 | 9/1991 | Deaton | 430/605 |
| 5,049,485 | 9/1991 | Deaton | 430/605 |
| 5,220,030 | 6/1993 | Deaton | 548/105 |
| 5,252,455 | 10/1993 | Deaton | 430/605 |
| 5,391,727 | 2/1995 | Deaton | 540/1 |
| 5,620,841 | 4/1997 | Lok et al. | 430/600 |
| 5,686,236 | 11/1997 | Lok et al. | 430/600 |
| 5,700,631 | 12/1997 | Lok et al. | 430/605 |

*Primary Examiner*—Mark F. Huff
*Attorney, Agent, or Firm*—Sarah Meeks Roberts

[57] ABSTRACT

A photographic element comprising a support having situated thereon a silver halide emulsion layer, said emulsion layer comprising a compound of the formula:

$$Z—S—Au(I)—S—Q \qquad (I)$$

wherein

Z represents an alkyl, aryl, or heterocyclic group; and

Q represents a heterocyclic group wherein S and Q together represent a mesoionic group.

24 Claims, No Drawings

AU(I) SENSITIZERS FOR SILVER HALIDE EMULSIONS

FIELD OF THE INVENTION

This invention relates to new Au(I) compounds, and to silver halide photographic elements containing such compounds. It further relates to the use of such compounds as sensitizers in silver halide photographic elements and methods of preparing silver halide emulsions containing such compounds.

BACKGROUND OF THE INVENTION

For more than a century, it has been known that certain materials are sensitive to actinic radiation and, upon exposure to such radiation, form latent images capable of being subsequently developed into useful visible images. Almost exclusively, commercial application of these radiation sensitive materials has been the domain of silver halides which exhibit superior sensitivity to light over other radiation sensitive materials, some of which have been known for as long as silver halides have been in use. Such superior sensitivity has made silver halides more practical for use in cameras and other photographic equipment since they can be utilized in low light situations, or in situations where the mechanical characteristics of a camera (or other exposure means) would interfere with an optimum exposure.

Despite their superior sensitivity to light, there nevertheless has been considerable effort devoted to improving the sensitivity of silver halide crystals, and hence the photographic elements in which they are contained. In this regard, photographic chemists have attempted to vary the processes for making, or the components within, silver halide emulsions. One particularly preferred means by which to improve sensitivity has been to chemically sensitize photographic emulsions with one or more compounds containing labile atoms of gold, sulfur, selenium or the like. Examples of chemically sensitized photographic silver halide emulsion layers are described in, for example, *Research Disclosure*, Item No. 308119, December 1989, Section III, and the references listed therein. (*Research Disclosure* is published by Kenneth Mason Publications Ltd, Dudley Annex, 12a North Street, Emsworth, Hampshire PO 10 7DQ, England.)

Among the Au(I) chemical sensitizers known in the industry, trisodium aurous dithiosusulfate is often cited as being advantageous. This compound, however, is not universally applicable to all emulsion systems because of certain disadvantages it provides. In particular, trisodium aurous dithiosulfate contains two thiosulfate ions that are bonded to gold. These ions may undergo sulfur sensitization reactions in addition to the gold sensitization reactions in the emulsion. Therefore, this Au(I) compound is not appropriate in silver halide compositions in which a ratio of sulfur to gold of less than 2:1 is desired for chemical sensitization, and also not appropriate in silver halide compositions in which sulfur or selenium sensitizers other than thiosulfate are desired.

Other known Au(I) chemical sensitizers include aurous sulfides and the Au(I) thiolate compounds as described in U.S. Pat. No. 3,503,749. With respect to the former, although relatively easy to manufacture, they have been known to provide considerable sensitization variability and thus more predictable alternatives are desired. With respect to the latter compounds, they contain a sulfonic acid substituent on the thiolate ligand to impart water solubility. Further, they require the use of gold fulminate in their manufacture, a compound that is dangerously explosive and thus not desirable for practical use.

U.S. Pat. No. 5,049,485 describes a new class of Au(I) compounds comprising mesoionic ligands. Specifically, the Au(I) compounds contain one or two mesoionic substituents bound directly to a gold atom. The compounds are also positively charged, and thus must be associated with an appropriate anion, typically a halogen or tetrafluoroborate. The compounds described in U.S. Pat. No. 5,049,485 are advantageous in that they provide Au(I) sensitization without many of the disadvantages inherent in the use of the aforementioned Au(I) compounds. However, they have been known to exhibit limited stability in solution or dispersion. Further, at certain levels and under certain photographic conditions, they can cause an undesirable increase in fog.

Various other Au(I) compounds have been described. U.S. Pat. Nos. 5,252,455 and 5,391,727 disclose the use of bis Au(I) bidentate macrocyclic cationic sensitizers. U.S. Pat. No. 5,049,484 teaches the use of bis Au(I) sensitizers wherein the Au atom is ligated to the nitrogen atoms of two heterocyclic rings. U.S. Pat. No. 5,220,030 teaches the use of Au(I) compounds with bis mesoionic heterocycles. U.S. Pat. No. 5,620,841 discloses the use of gelatin dispersions of Au(I) thiosulfonato sensitizers with two different ligands comprising at least one ligand that is mesoionic. There is increasing evidence that the bis mesoionic sensitizers lack solution stability such that they require refrigeration to prevent decomposition. There are also difficulties in the preparation of the starting materials and the mesoionic ligand for such compounds. In general, the ligands of all of these bis Au(I) compounds are somewhat difficult to make. U.S. Pat. No. 5,700,631 teaches the use of gelatin dispersions of Au(I) thiosulfonato sensitizer with two different ligands comprising at least one ligand that is a thioether group.

There is still need for a Au (I) compound that can provide chemical sensitization without a concurrent and substantial rise in fog levels. These compounds should be stable in solution or dispersion and should be suitable for multiple types of emulsion systems. Further, they should be readily synthesizable in the absence of dangerous and unstable reactants.

SUMMARY OF THE INVENTION

This invention provides a compound of the formula:

$$Z-S-Au(I)-S-Q \qquad (I)$$

wherein

Z represents an alkyl, aryl, or heterocyclic group; and
Q represents a heterocyclic group wherein S and Q together represent a mesoionic group. It further provides a photographic element comprising a support having situated thereon a silver halide emulsion layer, said emulsion layer comprising such compounds. It also provides a photographic element comprising a support having situated thereon a silver halide emulsion layer, said emulsion layer having been chemically sensitized in the presence of such compounds. Additionally it provides a method of preparing a silver halide emulsion comprising precipitating silver halide grains in an aqueous colloidal medium to form an emulsion, heating the emulsion, and adding to the emulsion, either before or during heating, the above Au(I) compounds.

The present invention provides novel Au(I) sensitizers for silver halide emulsions. The Au(I) compounds also offer improved stability. They are effective sensitizers without a concurrent and substantial rise in fog. The Au(I) compounds may be manufactured from inexpensive and commercially available starting materials and the ease of their preparation reduces the cost of manufacturing of the silver halide photographic element. Another advantage is that the preparation of the Au(I) compounds of the invention avoids the use of dangerous and unstable starting materials.

DETAILED DESCRIPTION OF THE INVENTION

The Au(I) compounds of this invention are represented by the following formula:

wherein
Z represents a substituted or unsubstituted alkyl, aryl, or heterocyclic group; and
Q represents a substituted or unsubstituted heterocyclic group which, when combined with the sulfur atom to which it is attached, is a mesoionic group. Z does not form a mesoionic group.

By alky, aryl, or heterocyclic group, in either the description of Z or Q, it is meant such groups as defined in accordance with the definitions set forth in Grant and Hackh's *Chemical Dictionary*, fifth ed., McGraw-Hill 1987, and in accordance with general rules of chemical nomenclature.

Preferably, the alkyl groups are substituted or unsubstituted groups having from 1 to 5 carbon atoms, although groups having as many as 20 carbon atoms or more are specifically contemplated. Exemplary alkyl groups include methyl, ethyl, propyl, butyl, pentyl, hexyl, octyl, nonyl, decyl, dodecyl, hexadecyl, octadecyl, isopropyl, and t-butyl.

It is preferred that the aryl groups are substituted or unsubstituted groups having from 6 to 20 carbon atoms and more preferably 6 to 10 carbon atoms. Exemplary aryl groups include phenyl, tolyl, naphthyl, biphenyl, azulenyl, anilinyl, and anisidinyl. Most preferred are groups selected from phenyl, tolyl, and naphthyl.

Preferably the heterocyclic groups are substituted or unsubstituted 5-to 18-membered rings, at least one heteroatom choosen from oxygen, nitrogen or sulfur. More preferred are 5- to 6- membered rings having at least one nitrogen heteroatom, and preferably more than one nitrogen heteroatom. Exemplary heterocyclic groups (which include heteroaryl groups) include pyrrolyl, furanyl, tetrahydrofuranyl, pyridinyl, picolinyl, piperidinyl, morpholinyl, thiadiazolyl, thiatriazolyl, benzothiazolyl, benzoxazolyl, benzimidizolyl, benzoselenozolyl, benzotriazolyl, indazolyl, quinolinyl, quinaldinyl, pyrrolidinyl, thiophenyl, oxazolyl, thiazolyl, imidazolyl, selenazolyl, tellurazolyl, triazolyl, tetrazolyl, and oxadiazolyl. It is preferred that the heterocyclic groups be selected from triazolyl, tetrazolyl and thiazolyl.

In a preferred embodiment of the invention, the Au(I) compound is of the formula:

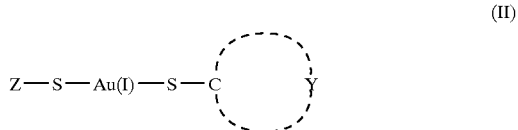

wherein Z is as defined above, and Y represents the atoms necessary for forming a 5 to 18 atom heterocyclic group, which when combined with the sulfur atom to which it is attached, is a mesoionic group.

The mesoionic group formed by S—Q is more preferably of the formula:

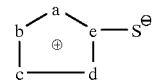

wherein the + sign with a circle around it in the heterocyclic ring symbolizes six delocalized π electrons associated with a positive charge on the heterocyclic ring. The a, b, c, d, and e represent the unsubstituted or substituted atoms necessary to complete the mesoionic compound, for example the carbon and nitrogen atoms necessary to complete a mesoionic triazolium or tetrazolium 5-member heterocyclic ring. The members of the heterocyclic ring (a, b, c, d, and e) may be CR or NR' groups or chalcogen atoms. The minus sign indicates two additional electrons on the exocyclic group S⁻ which are conjugated with the six π electrons on the heterocyclic ring. It is understood that there is extensive delocalization. The groups R and R' may be hydrogen atoms, substituted or unsubstituted alkyl, aryl, or heterocyclic groups, or R and R' may link together by bonding to form another ring. It is through the exocyclic group S⁻ that the mesoionic compound coordinates to Au(I).

The preferred Au(I) compounds are of the formula:

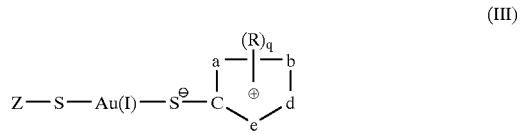

wherein
Z is as defined above;
a, b, d, and e represent atoms necessary to complete the heterocyclic group and are independently selected from carbon, nitrogen or chalcogen atoms, at least one of a, b, d, or e being nitrogen;
R is independently hydrogen or an alkyl, aryl, or heterocyclic group, preferably hydrogen or an alkyl or aryl group having from 1 to 8 carbon atoms; and
q is from 1 to 4, preferably 2 or 3.

It is to be understood in such a compound that a balancing charge to the sulfur atom's negative charge is associated with the heterocyclic ring as represented by a, b, c, d and e (and is represented by the + charge with a circle around it in the heterocyclic group). Thus, the heterocycle, in combination with the sulfur to which it is bound, represents a mesoionic group as described above.

In a more preferred embodiment of the invention, the Au(I) compound is of the formula:

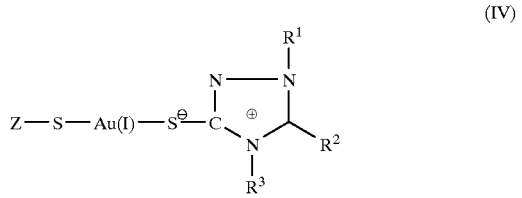

wherein Z is as defined above, and R¹, R², and R³ are independently selected from hydrogen or an alkyl group having from 1 to 5 carbon atoms. Again, the heterocycle and sulfur atom are taken together to be a mesoionic group, with the positive charge, in this instance, residing on one of the nitrogen atoms.

Unless otherwise specifically stated, substituent groups which may be substituted on molecules herein include any groups, whether substituted or unsubstituted, which do not destroy properties necessary for photographic utility. When the term "group" is applied to the identification of a substituent containing a substitutable hydrogen, it is intended to encompass not only the substituent's unsubstituted form, but also its form further substituted with any group or groups as herein mentioned. Suitably, the group may be bonded to the remainder of the molecule by an atom of carbon, silicon, oxygen, nitrogen, phosphorous, or sulfur. Suitable substituents for A include, for example, halogen, such as chlorine, bromine or fluorine; nitro; hydroxyl; cyano; carboxyl; or groups which may be further substituted, such as alkyl, including straight or branched chain alkyl, such as methyl, trifluoromethyl, ethyl, t-butyl, 3-(2,-dit-pentylphenoxy) propyl, and tetradecyl; alkenyl, such as ethylene, 2-butene; alkoxy, such as methoxy, ethoxy, propoxy, butoxy, 2-methoxyethoxy, sec-butoxy, hexyloxy, 2-ethylhexyloxy, tetradecyloxy, 2-(2,4-di-t-pentylphenoxy)ethoxy, and 2-dodecyloxyethoxy; aryl such as phenyl, 4-t-butylphenyl, 2,4,6-trimethylphenyl, naphthyl; aryloxy, such as phenoxy, 2-methylphenoxy, alpha- or beta-naphthyloxy, and 4-tolyloxy; carbonamido, such as acetamido, benzamido, butyramido, tetradecanamido, alpha-(2,4-di-t-pentyl-phenoxy)acetamido, alpha-(2,4-di-t-pentylphenoxy) butyramido, alpha-(3-pentadecylphenoxy)-hexanamido, alpha-(4-hydroxy-3-t-butylphenoxy)-tetradecanamido, 2-oxo-pyrrolidin-1-yl, 2-oxo-5-tetradecylpyrrolin-1-yl, N-methyltetradecanamido, N-succinimido, N-phthalimido, 2,5-dioxo-1-oxazolidinyl, 3-dodecyl-2,5-dioxo-1-imidazolyl, and N-acetyl-N-dodecylamino, ethoxycarbonylamino, phenoxycarbonylamino, benzyloxycarbonylamino, hexadecyloxycarbonylarnino, 2,4-di-t-butylphenoxycarbonylamino, phenylcarbonylamino, 2,5-(di-t-pentylphenyl) carbonylamino, p-dodecyl-phenylcarbonylamino, p-toluylcarbonylamino, N-methylureido, N,N-dimethylureido, N-methyl-N-dodecylureido, N-hexadecylureido, N,N-dioctadecylureido, N,N-dioctyl-N'-ethylureido, N-phenylureido, N,N-diphenylureido, N-phenyl-N-p-toluylureido, N-(m-hexadecylphenyl)ureido, N,N-(2,5-di-t-pentylphenyl)-N'-ethylureido, and t-butylcarbonamido; sulfonamido, such as methylsulfonamido, benzenesulfonamido, p-toluylsulfonamido, p-dodecylbenzenesulfonamido, N-methyltetradecylsulfonamido, N,N-dipropyl-sulfamoylamino, and hexadecylsulfonamido; sulfamoyl, such as N-methylsulfamoyl, N-ethylsulfamoyl, N,N-dipropylsulfamoyl, N-hexadecylsulfamoyl, N,N-dimethylsulfamoyl; N-[3-(dodecyloxy)propyl]sulfamoyl, N-[4-(2,4-di-t-pentylphenoxy)butyl]sulfamoyl, N-methyl-N-tetradecylsulfamoyl, and N-dodecylsulfamoyl; carbamoyl, such as N-methylcarbamoyl, N,N-dibutylcarbamoyl, N-octadecylcarbamoyl, N-[4-(2,4-di-t-pentylphenoxy)butyl]carbamoyl, N-methyl-N-tetradecylcarbamoyl, and N,N-dioctylcarbamoyl; acyl, such as acetyl, (2,4-di-t-amylphenoxy)acetyl, phenoxycarbonyl, p-dodecyloxyphenoxycarbonyl methoxycarbonyl, butoxycarbonyl, tetradecyloxycarbonyl, ethoxycarbonyl, benzyloxycarbonyl, 3-pentadecyloxycarbonyl, and dodecyloxycarbonyl; sulfonyl, such as methoxysulfonyl, octyloxysulfonyl, tetradecyloxysulfonyl, 2-ethylhexyloxysulfonyl, phenoxysulfonyl, 2,4-di-t-pentylphenoxysulfonyl, methylsulfonyl, octylsulfonyl, 2-ethylhexylsulfonyl, dodecylsulfonyl, hexadecylsulfonyl, phenylsulfonyl, 4nonylphenylsulfonyl, and p-toluylsulfonyl; sulfonyloxy, such as dodecylsulfonyloxy, and hexadecylsulfonyloxy; sulfmyl, such as methylsulfinyl, octylsulfinyl, 2-ethylhexylsulfinyl, dodecylsulfinyl, hexadecylsulfinyl, phenylsulfinyl, 4-nonylphenylsulfinyl, and p-toluylsulfinyl; thio, such as ethylthio, octylthio, benzylthio, tetradecylthio, 2-(2,4-di-t-pentylphenoxy) ethylthio, phenylthio, 2-butoxy-5-t-octylphenylthio, and p-tolylthio; acyloxy, such as acetyloxy, benzoyloxy, octadecanoyloxy, p-dodecylamidobenzoyloxy, N-phenylcarbamoyloxy, N-ethylcarbamoyloxy, and cyclohexylcarbonyloxy; amine, such as phenylanilino, 2-chloroanilino, diethylamine, dodecylamine; irnino, such as 1 (N-phenylimido)ethyl, N-succinimido or 3-benzylhydantoinyl; phosphate, such as dimethylphosphate and ethylbutylphosphate; phosphite, such as diethyl and dihexylphosphite; a heterocyclic group, a heterocyclic oxy group or a heterocyclic thio group, each of which may be substituted and which contain a 3 to 7 membered heterocyclic ring composed of carbon atoms and at least one hetero atom selected from the group consisting of oxygen, nitrogen and sulfur, such as 2-furyl, 2-thienyl, 2-benzimidazolyloxy or 2-benzothiazolyl; quaternary ammonium, such as triethylammonium; and silyloxy, such as trimethylsilyloxy. Preferred substituents are alkyl groups with 1 to 4 carbons.

Generally, the above groups and substituents thereof may include those having up to 48 carbon atoms, typically 1 to 36 carbon atoms and usually less than 24 carbon atoms, but greater numbers are possible depending on the particular substituents selected.

Examples of these novel Au(I) sensitizers include but are not limited to the following:

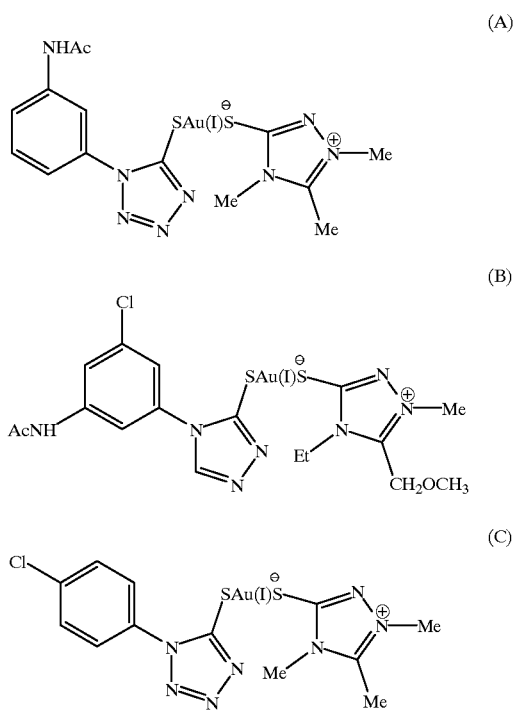

-continued
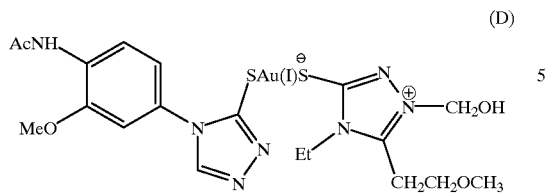
(D)
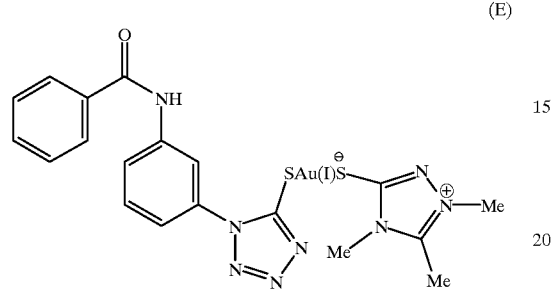
(E)
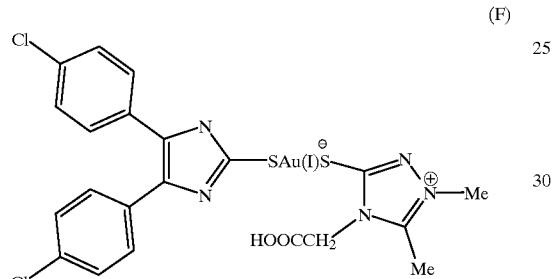
(F)
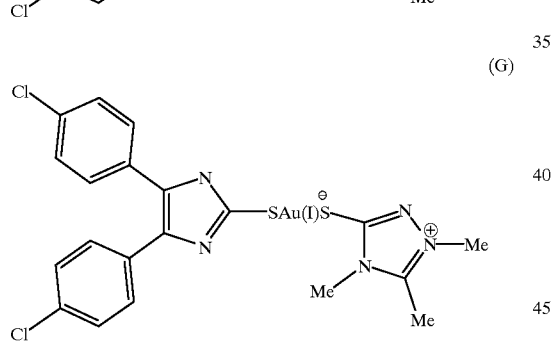
(G)
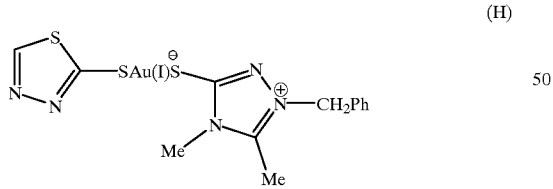
(H)
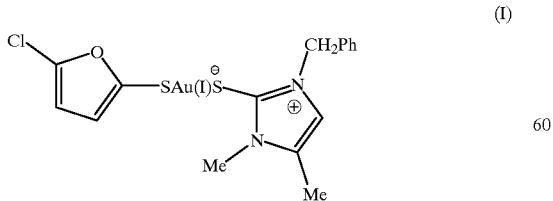
(I)
-continued
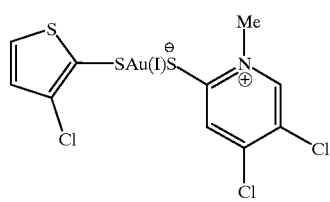
(J)
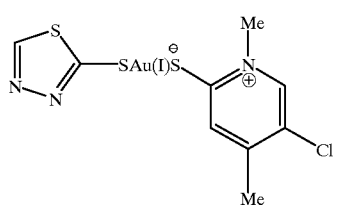
(K)
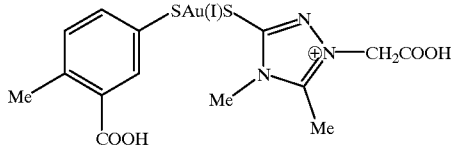
(L)
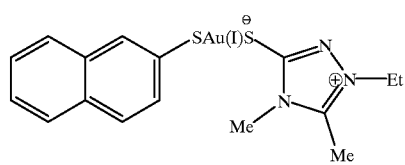
(M)
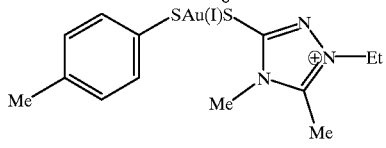
(N)
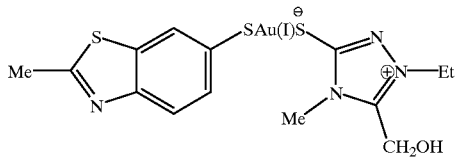
(O)
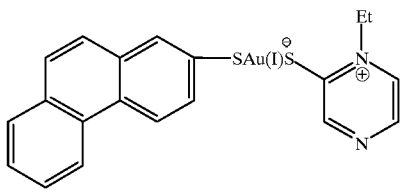
(P)

-continued (Q)
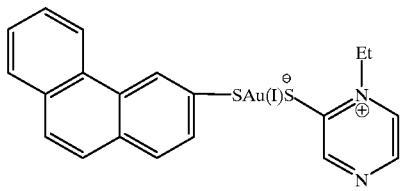

(R)
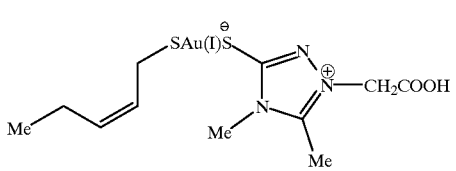

(S)
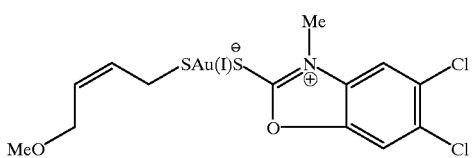

(T)
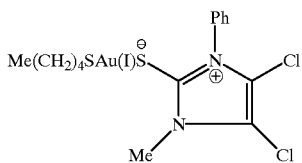

(U)
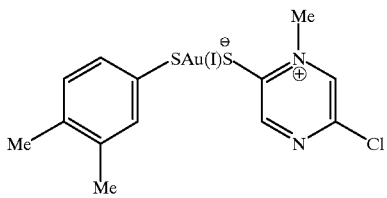

(V)
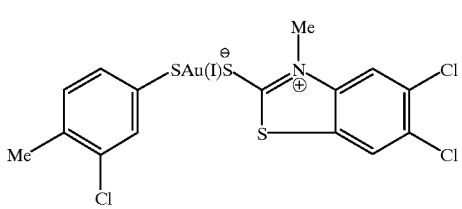

(W)
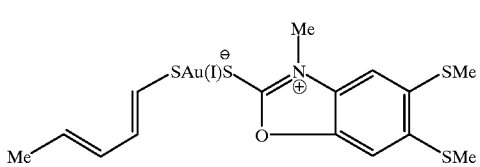

-continued (X)
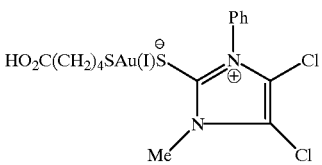

The mercapto-mercaptomesoionic Au(I) complexes may be made from the bis Au(I) complex of the mercaptomesoionic heterocycle tetrafluoroborate salt. This is usually done by dissolving the latter in hot water and then adding a solution of the sodium mercaptide to the Au(I) complex.

A preferred method of synthesis requires that the bis Au(I) compounds of Deaton, U.S. Pat. No. 5,049,485, such patent being incorporated herein by reference, be reacted with a mercaptan ligand having a stronger affinity for the Au(I) atom than one of the mesoionic groups. Such a mercaptan ligand effectively displaces one of the mesoionic groups thus forming a compound as utilized in the present invention. Mercaptans are readily available materials. They may be synthesized from standard text books or they may be commercially available. Likewise, mesoionic mercapto heterocycles have been prepared from established procedures.

Levels of the Au(I) compounds which may be utilized range from about 0.01 $\mu$mol to 10,000 $\mu$mol per silver mole; preferably from about 0.05 $\mu$mol to 1,000 $\mu$mol per silver mole; more preferably from about 0.1 $\mu$mol to 500 $\mu$mol per silver mole and most preferably from about 1 $\mu$mol to 50 $\mu$mol/Ag mole.

The photographic emulsions of this invention are generally prepared by precipitating silver halide crystals in a colloidal matrix by methods conventional in the art. The colloid is typically a hydrophilic film forming agent such as gelatin, alginic acid, or derivatives thereof.

The crystals formed in the precipitation step are washed and then chemically and spectrally sensitized by adding spectral sensitizing dyes and chemical sensitizers, and by providing a heating step during which the emulsion temperature is raised, typically from 40° C. to 70° C., and maintained for a period of time. The precipitation and spectral and chemical sensitization methods utilized in preparing the emulsions employed in the invention can be those methods known in the art.

Chemical sensitization of the emulsion typically employs sensitizers such as: sulfur-containing compounds, e.g., allyl isothiocyanate, sodium thiosulfate and allyl thiourea; reducing agents, e.g., polyamines and stannous salts; noble metal compounds, e.g., gold, platinum; and polymeric agents, e.g., polyalkylene oxides. As described, heat treatment is employed to complete chemical sensitization. Spectral sensitization is effected with a combination of dyes, which are designed for the wavelength range of interest within the visible or infrared spectrum. It is known to add such dyes both before and after heat treatment.

After spectral sensitization, the emulsion is coated on a support. Various coating techniques include dip coating, air knife coating, curtain coating and extrusion coating.

The Au(I) compounds may be added to the silver halide emulsion at any time during the preparation of the emulsion, i.e., during precipitation, during or before chemical sensitization or during final melting and co-mixing of the emulsion and additives for coating. Preferably, the emulsion is chemically sensitized in the presence of the Au(I) compounds. More preferably, these compounds are added after precipitation of the grains, and most preferably they are added before or during the heat treatment of the chemical sensitization step.

The Au(I) compounds may be introduced into the emulsion at the appropriate time by any of the various techniques known to those skilled in the art. Preferably they are added as a gel dispersion. One suitable method includes preparing a silver halide emulsion by precipitating silver halide grains in an aqueous colloidal medium to form an emulsion, digesting (heating) the emulsion, preferably at a temperature in the range of 40 to 80° C., and adding to the emulsion, either before or during heating, a gel dispersion of the Au(I) compound. In one preferred embodiment the emulsion is also sensitized with thiosulfate pentahydrate (hypo).

Conditions for sensitizing silver halide grains such a pH, pAg, and temperature are not particularly limited. The pH is generally about 1 to 9, preferably about 3 to 6, and pAg is generally about 5 to 12, preferably from about 7 to 10.

The Au(I) compounds may also be added to the vessel containing the aqueous gelatin salt solution before the start of the precipitation; or to a salt solution during precipitation. Other modes are also contemplated. Temperature, stirring, addition rates and other precipitation factors may be set within conventional ranges, by means known in the art, so as to obtain the desired physical characteristics.

The Au(I) compounds may be used in addition to any conventional sensitizers as commonly practiced in the art. Combinations of more than one Au(I) compound may be utilized.

The silver halide emulsions utilized in this invention may be comprised of any halide distribution. Thus, they may be comprised of silver bromoiodide, silver chloride, silver bromide, silver bromochloride, silver chlorobromide, silver iodochloride, silver iodobromide, silver bromoiodochloride, silver chloroiodobromide, silver iodobromochloride, and silver iodochlorobromide emulsions. In one embodiment silver bromoiodides with various morphologies and halide compositions may be utilized. Preferably, the silver halide emulsions utilized in this invention are predominantly silver chloride emulsions. By predominantly silver chloride, it is meant that the grains of the emulsion are greater than about 50 mole percent silver chloride. Preferably, they are greater than about 90 mole percent silver chloride; and optimally greater than about 95 mole percent silver chloride. These emulsions may contain iodides or bromides or both as the remainder of the total halide composition.

The silver halide emulsions can contain grains of any size and morphology. Thus, the grains may take the form of cubes, octahedrons, cubo-octahedrons, or any of the other naturally occurring morphologies of cubic lattice type silver halide grains. Further, the grains may be irregular such as spherical grains or tabular grains. Grains having a tabular or cubic morphology are preferred. Tetradecahedral grains with {111} and {100} crystal faces may also be utilized. The Au(I) compounds may also be used in reversal systems having core shell silver halide emulsions.

The photographic emulsions may be incorporated into color negative particularly color paper) or reversal photographic elements. The photographic element may also comprise a transparent magnetic recording layer such as a layer containing magnetic particles on the underside of a transparent support, as described in *Research Disclosure,* November 1992, Item 34390 published by Kenneth Mason Publications, Ltd., Dudley Annex, 12a North Street, Emsworth, Hampshire PO10 7DQ, ENGLAND. Typically, the element will have a total thickness (excluding the support) of from about 5 to about 30 microns. Further, the photographic elements may have an annealed polyethylene naphthalate film base such as described in Hatsumei Kyoukai Koukai Gihou No. 94-6023, published Mar. 15, 1994 (Patent Office of Japan and Library of Congress of Japan) and may be utilized in a small format system, such as described in *Research Disclosure,* June 1994, Item 36230 published by Kenneth Mason Publications, Ltd., Dudley Annex, 12a North Street, Emsworth, Hampshire POIO 7DQ, ENGLAND, and such as the Advanced Photo System, particularly the Kodak ADVANTIX films or cameras.

In the following Table, reference will be made to (1) *Research Disclosure,* December 1978, Item 17643, (2) *Research Disclosure,* December 1989, Item 308119, (3) *Research Disclosure,* September 1994, Item 36544, and (4) *Research Disclosure,* September 1996, Item 38957, all published by Kenneth Mason Publications, Ltd., Dudley Annex, 12a North Street, Emsworth, Hampshire PO10 7DQ, ENGLAND, the disclosures of which are incorporated herein by reference. The Table and the references cited in the Table are to be read as describing particular components suitable for use in the elements of the invention. The Table and its cited references also describe suitable ways of preparing, exposing, processing and manipulating the elements, and the images contained therein. Photographic elements and methods of processing such elements particularly suitable for use with this invention are described in *Research Disclosure,* February 1995, Item 37038, published by Kenneth Mason Publications, Ltd., Dudley Annex, 12a North Street, Emsworth, Hampshire PO10 7DQ, ENGLAND, the disclosure of which is incorporated herein by reference.

| Reference | Section | Subject Matter |
|---|---|---|
| 1 | I, II | Grain composition, |
| 2 | I, II, IX, X, XI, XII, XIV, XV | morphology and preparation. Emulsion preparation including |
| 3 & 4 | I, II, III, IX A & B | hardeners, coating aids, addenda, etc. |
| 1 | III, IV | Chemical sensitization and |
| 2 | III, IV | spectral sensitization/ |
| 3 & 4 | IV, V | desensitization |
| 1 | V | UV dyes, optical |
| 2 | V | brighteners, luminescent |
| 3 & 4 | VI | dyes |
| 1 | VI | Antifoggants and |
| 2 | VI | stabilizers |
| 3 & 4 | VII | |
| 1 | VIII | Absorbing and scattering |
| 2 | VIII, XIII, XVI | materials; Antistatic layers; matting agents |
| 3 & 4 | VIII, IX C & D | |
| 1 | VII | Image-couplers and image- |
| 2 | VII | modifying couplers; Wash- |
| 3 & 4 | X | out couplers; Dye stabilizers and hue modifiers |
| 1 | XVII | Supports |
| 2 | XVII | |
| 3 & 4 | XV | |
| 3 & 4 | XI | Specific layer arrangements |
| 3 & 4 | XII, XIII | Negative working emulsions; Direct positive emulsions |
| 2 | XVIII | Exposure |
| 3 & 4 | XVI | |

-continued

| Reference | Section | Subject Matter |
|---|---|---|
| 1 | XIX, XX | Chemical processing; |
| 2 | XIX, XX, XXII | Developing agents |
| 3 & 4 | XVIII, XIX, XX | |
| 3 & 4 | XIV | Scanning and digital processing procedures |

The photographic elements can be incorporated into exposure structures intended for repeated use or exposure structures intended for limited use, variously referred to as single use cameras, lens with film, or photosensitive material package units.

The photographic elements can be exposed with various forms of energy which encompass the ultraviolet, visible, and infrared regions of the electromagnetic spectrum as well as the electron beam, beta radiation, gamma radiation, X-ray, alpha particle, neutron radiation, and other forms of corpuscular and wave-like radiant energy in either noncoherent (random phase) forms or coherent (in phase) forms, as produced by lasers. When the photographic elements are intended to be exposed by X-rays, they can include features found in conventional radiographic elements. The photographic elements are preferably exposed to actinic radiation, typically in the visible region of the spectrum, to form a latent image, and then processed to form a visible dye image. Development is typically followed by the conventional steps of bleaching, fixing, or bleach-fixing, to remove silver or silver halide, washing, and drying.

The following examples are intended to illustrate, but not limit, the invention.

EXAMPLES

Example 1

Synthesis of 1-(3-acetamidophenyl)-5-mercaptotetrazole 1,4,5-trimethyl-1,2,4-triazolium-3-thiolate Au(I) (Compound A)

To a solution of bis (1,4,5-trimethyl-1,2,4-triazolium-3-thiolate) Au(I) tetrafluoroborate (ZZ, 1.5 g) (prepared as taught in U.S. Pat. No. 5,220,030 incorporated herein by reference) in warm distilled water (200 mL) was added with stirring a solution of the sodium salt of 1-(3-acetamidophenyl)-5-mercaptotetrazole (0.6766 g) in 20 mL of distilled water. The mixture was filtered, washed with water and then dried to constant weight. The weight of solid was 1.18 g or a yield of 78%. Component analysis of compound yields the following data: Au: 34.80%, C: 28.82%, S: 10.59%, H:3.02%, N: 19.17. Calculated values are: Au: 34.29%, C: 29.27%, S: 11.16%, H: 2.98%, N: 19.51. Thermogravimetric analysis, infrared analysis and X-diffraction patterns were all consistent with the structure of A.

Synthesis of Compound A in a gelatin dispersion

A solution of the sodium salt of 1-(3-acetamidophenyl)-5-mercaptotetrazole (2.41 g) was made by dissolving the solid in 160 mL of distilled water at 45° C. This solution was added to a dispersion made with 307.2 g of gelatin (12.5%) in a 4 L beaker at 45° C. To this gelatin dispersion was added slowly with stirring, a solution of bis (1,4,5-trimethyl-1,2, 4-triazolium-3-thiolate) Au(I) tetrafluoroborate (5.35 g) dissolved in distilled water (525 g) at 70° C. The mixture was stirred rapidly for another two minutes before it was chilled to 25° C. Finally the temperature was lowered to 10° C. without further stirring. The weight of the dispersion was 967 g with gold calculated at 1.85 g per Kg of gel dispersion or 5.39 g of Compound A per Kg of dispersion.

Preparation of sodium salt of 1-(3-acetamidophenyl)-5-mercaptotetrazole(Compound OO) and (1,4,5-trimethyl-1,2, 4-triazolium-3-thiolate) (Compound TTT) in gelatin dispersion A solution of Compound QQ (2.41 g in 160 mL of distilled water) was added to a gelatin dispersion (307.2 g of 12.5% gelatin) in a 4 L beaker at 45° C. To this gelatin dispersion was added slowly with stirring a solution of Compound TTT (2.69 g) in warm distilled water (528 g). The mixture was stirred rapidly for another two minutes before it was chilled to 25° C. Finally the temperature was lowered to 10° C. without further stirring. Weight of dispersion was 978 g.

Example 2

In accordance with the present invention, a 0.3 mole cubic negative silver chloride emulsion was sensitized at 40° C. with p-glutaramidophenyl disulfide (10 mg/Ag mol) with hypo (7.42 mg/Ag mol) and Compound A or comparison Compounds ZZ, QQ or TTT as indicated in Table 1. The emulsion was heated to 60° C. at a rate of 20° C. per 17 minutes and then held at this temperature for 52 minutes. During this time, 1-(3-acetamidophenyl)-5-mercaptotetrazole (297 mg/Ag mol), potassium hexachloroiridate (0.121 mg/Ag mol) and potassium bromide (1359 mg/Ag mol) were added. The emulsion was cooled down to 40° C. at a rate of 20° C. per 17 minutes. At this time, a red spectral sensitizing dye, anhydro-3-ethyl-9,1 1-neopentylene-3'-(3-sulfopropyl)thiadicarbocyanine hydroxide (12 mg/Ag mol), was added and the pH of the emulsion adjusted to 6.0. The emulsion thus sensitized also contained a cyan dye-forming coupler 2-(alpha (2,4-di-tert-amyl-phenoxy) butyramido)4,6-dichloro-5-ethyl phenol (0.42 g/m$^2$) in di-n-butyl phthalate coupler solvent (0.429 g/m$^2$) and gelatin (1.08 g/m$^2$). The emulsion (0.18 g Ag/m$^2$) was coated on a resin coated paper support and 1.076 g/m$^2$ gel overcoat was applied as a protective layer along with the hardener bis (vinylsulfonyl) methyl ether in an amount of 1.8% of the total gelatin weight.

The coatings were given a 0.1 second exposure, using a 0–3 step tablet (0.15 increments) with a tungsten lamp designed to stimulate a color negative print exposure source. This lamp had a color temperature of 3000K, log lux 2.95, and the coatings were exposed through a combination of magenta and yellow filters, a 0.3 ND (Neutral Density), and a UV filter. The processing consisted of a color development (45 sec, 35° C.), bleach-fix (45 sec, 35° C.) and stabilization or water wash (90 sec, 35° C.) followed by drying (60 sec, 60° C.). The chemistry used in the Colenta processor consisted of the following solutions:

| Developer: | | |
|---|---|---|
| Lithium salt of sulfonated polystyrene | 0.25 | mL |
| Triethanolamine | 11.0 | mL |
| N,N-diethylhydroxylamine (85% by wt.) | 6.0 | mL |
| Potassium sulfite (45% by wt.) | 0.5 | mL |
| Color developing agent (4-(N-ethyl-N-2-methanesulfonyl aminoethyl)-2-methyl-phenylenediaminesesquisulfate mondhydrate | 5.0 | g |
| Stilbene compound stain reducing agent | 2.3 | g |
| Lithium sulfate | 2.7 | g |
| Potassium chloride | 2.3 | g |
| Potassium bromide | 0.025 | g |
| Sequestering agent | 0.8 | mL |

-continued

| | | |
|---|---|---|
| Potassium carbonate | 25.0 | g |
| Water to total of 1 liter, pH adjusted to 10.12 | | |
| Bleach-fix | | |
| Ammonium sulfite | 58 | g |
| Sodium thiosulfate | 8.7 | g |
| Ethylenediaminetetracetic acid ferric ammonium salt | 40 | g |
| Acetic acid | 9.0 | mL |
| Water to total 1 liter, pH adjusted to 6.2 | | |
| Stabilizer | | |
| Sodium citrate | 1 | g |
| Water to total 1 liter, pH adjusted to 7.2. | | |

The speed taken at the 1.0 density point of the D log E curve was taken as a measure of the sensitivity of the emulsion. Dmin was measured as the minimum density above zero. Toe at 0.5 was taken as the density at 0.5 log E fast of the density point of 1.0. Toe at 0.3 was taken as the density at 0.3 log E fast of the density point of 1.0. Shoulder was taken as the density at 0.5 log E slow of the density point of 1.0. Gamma is the slope of the line between the density points that are 0.3 log E faster and 0.3 log E slower than the density point at 1.0. Dmax is the maximum density of the D log E curve.

1.5× level), softer 0.5 toe (higher toe values) and lower contrast (lower gamma values) than did inventive Compound A.

Example 3

In another practice of the invention, a 0.3 mol of an negative silver chloride emulsion was sensitized at 40° C. with a green spectral sensitizing dye, 5-chloro-2-[2-[[5-phenyl-3-(3-sulfobutyl)-2(3H)-benzoxazolylidene]methyl]-1-butenyl]-3-(3-sulfopropyl)-benzoxazolium sodium salt (379.45 mg/Ag mol), 0.28 mg/Ag mol of sodium thiosulfate pentahydrate (hypo), and Compound A or comparison Compounds ZZ, QQ or TTT at levels indicated in Table 2. The emulsion was heated to 60° C. at a rate of 10° C. per 6 minutes and then held at this temperature for 40 minutes. The emulsion was cooled to 40° C. at a rate of 10° C. per 6 minutes. At 40° C., solutions of 1-(3-acetamidophenyl)-5-mercaptotetrazole (200 mg/Ag mol) and potassium bromide (795 mg/Ag mol) were added to the emulsion. This emulsion was mixed further with a green dye-forming coupler 7-chloro-6-(1,1-dimethylethyl)-3-[3-(dodecylsulfonyl) propyl]-1H-pyrazolo[5, 1-c]-1,2,4-triazole (0.018 g/m$^2$) in di-n-butylphthalate coupler solvent and gelatin. The emulsion (0.102 g Ag/m$^2$) was coated on a resin coated paper support and an overcoat applied as a protective layer along with the hardener bis (vinylsulfonyl) methyl ether in an amount of 1.8% of the total gelatin weight. The emulsion (0.102 g Ag/m$^2$) was coated on a resin coated paper support and an overcoat applied as a protective layer along with the hardener bis (vinylsulfonyl) methyl ether in an amount of 1.8% of the total gelatin weight. The coatings were exposed and processed as for Example 2.

TABLE 1

| Sample | Compound | μmol Ag mol | Spd | Dmin | 0.5 Toe | 0.3 Toe | Shldr | Gamma | Dmax |
|---|---|---|---|---|---|---|---|---|---|
| 1 (comparison) | none | 0 | 76 | 0.089 | 0.368 | 0.672 | 1.218 | 0.910 | 1.840 |
| 2 (comparison) | QQTTT | 0.5 X | 79 | 0.100 | 0.260 | 0.545 | 1.331 | 1.311 | 2.068 |
| 3 (comparison) | QQ -TTT | 2.5 X | 90 | 0.103 | 0.153 | 0.302 | 1.683 | 2.301 | 2.314 |
| 4 (comparison) | ZZ | 1.5 X | 144 | 0.134 | 0.183 | 0.325 | 1.973 | 2.747 | 2.735 |
| 5 (comparison) | ZZ | 2.5 X | 136 | 0.112 | 0.225 | 0.400 | 1.698 | 2.163 | 2.698 |
| 6 (invention) | A | 0.25 X | 99 | 0.105 | 0.377 | 0.591 | 1.303 | 1.187 | 2.016 |
| 7 (invention) | A | 0.5 X | 109 | 0.103 | 0.330 | 0.558 | 1.425 | 1.446 | 2.175 |
| 8 (invention) | A | X | 136 | 0.099 | 0.178 | 0.370 | 1.644 | 2.122 | 2.584 |
| 9 (invention) | A | 1.5 X | 153 | 0.096 | 0.153 | 0.337 | 2.012 | 2.792 | 2.750 |
| 10 (invention) | A | 2.5 X | 141 | 0.111 | 0.180 | 0.355 | 1.891 | 2.560 | 2.703 |
| 11 (invention) | A | 3 X | 138 | 0.116 | 0.194 | 0.373 | 1.882 | 2.516 | 2.636 |

X = 27.27 μmol per Ag mol

It can be seen in Table 1 that samples 1 (without Compound A), 2, and 3 (without Compound A but with control compounds without gold, QQ and TTT) all have lower speed and show little sensitization. Samples of the present invention (6–11) which contain Compound A show much enhanced sensitivity. More specifically, sample 9 has the best combination of speed, toes (lower values indicate sharper toe), high shoulder and contrast. At comparable levels, Compound 22 showed lower speed, higher Dmin (at

TABLE 2

| Samples | Compound | μmol Ag mol | hypo | Spd | Dmin | 0.5 Toe | 0.3 Toe | Gamma | Shldr | Dmax |
|---|---|---|---|---|---|---|---|---|---|---|
| 12 (comparison) | none | — | Y | 78 | 0.093 | 0.228 | 0.393 | 2.552 | 1.924 | 2.592 |
| 13 (comparison) | QQ, TTT | 0.25 X | Y | 81 | 0.098 | 0.185 | 0.368 | 2.646 | 1.956 | 2.611 |
| 14 (comparison) | QQ, TTT | 3 X | Y | 81 | 0.095 | 0.176 | 0.361 | 2.726 | 1.997 | 2.647 |
| 15 (invention) | A | 0.25 X | Y | 89 | 0.099 | 0.242 | 0.410 | 2.543 | 1.936 | 2.607 |
| 16 (invention) | A | X | Y | 178 | 0.103 | 0.177 | 0.360 | 2.479 | 1.847 | 2.650 |
| 17 (invention) | A | 2 X | Y | 180 | 0.098 | 0.167 | 0.349 | 2.739 | 1.992 | 2.703 |
| 18 (invention) | A | 3 X | Y | 181 | 0.099 | 0.163 | 0.344 | 2.731 | 1.982 | 2.660 |
| 19 (comparison) | none | 0 | N | 76 | 0.098 | 0.179 | 0.358 | 2.737 | 2.000 | 2.651 |
| 20 (comparison) | ZZ | X | N | 81 | 0.094 | 0.195 | 0.370 | 2.636 | 1.952 | 2.631 |

TABLE 2-continued

| Samples | Compound | μmol Ag mol | hypo | Spd | Dmin | 0.5 Toe | 0.3 Toe | Gamma | Shldr | Dmax |
|---|---|---|---|---|---|---|---|---|---|---|
| 21 (comparison) | ZZ | 2 X | N | 79 | 0.095 | 0.208 | 0.377 | 2.630 | 1.955 | 2.633 |
| 22 (invention) | A | X | N | 85 | 0.096 | 0.225 | 0.396 | 2.547 | 1.924 | 2.629 |
| 23 (invention) | A | 2 X | N | 82 | 0.097 | 0.190 | 0.373 | 2.625 | 1.949 | 2.628 |

X = 7.02 μmol per Ag mol

The data in Table 2 show again that samples containing only the control compounds QQ and TTT without gold, (13, and 14) have no sensitizing effect relative to the coating with no sensitizer (sample 12). Samples containing the combination of Compound A and hypo (samples 15, 16, 17, 18) show speeds higher than the comparison coatings. For emulsions sensitized without hypo, the invention samples (22, 23), have a higher speed than the comparison emulsion sensitized with ZZ (samples 20, 21).

The invention has been described in detail with particular reference to certain preferred embodiments thereof, but it will be understood that variations and modifications can be effected within the spirit and scope of the invention.

What is claimed is:

1. A photographic element comprising a support having situated thereon a silver halide emulsion layer, said emulsion layer comprising a compound of the formula:

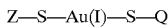   (I)

wherein

Z represents an alkyl, aryl, or heterocyclic group; and

Q represents a heterocyclic group wherein S and Q together represent a mesoionic group.

2. A photographic element according to claim 1 wherein the compound is of the formula:

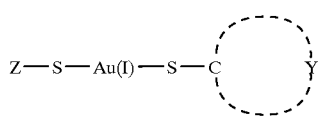   (II)

wherein Z is as defined in claim 1, and Y represents the atoms necessary for forming a 5 to 18 atom heterocyclic group.

3. A photographic element according to claim 2 wherein Y contains at least 1 nitrogen atom.

4. A photographic element according to claim 3 wherein the compound is of the formula:

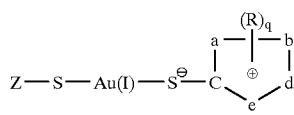   (III)

wherein

Z is as defined in claim 1;

a, b, d, and e represent atoms necessary to complete the heterocyclic group and are independently selected from carbon, nitrogen or chalcogen atoms, at least one of a, b, d, or e being nitrogen;

R is independently hydrogen or an alkyl, aryl, or heterocyclic group; and q is from 1 to 4.

5. A photographic element according to claim 4 wherein R is independently hydrogen or an alkyl or aryl group having from 1 to 8 carbon atoms.

6. A photographic element according to claim 5 wherein the compound is of the formula:

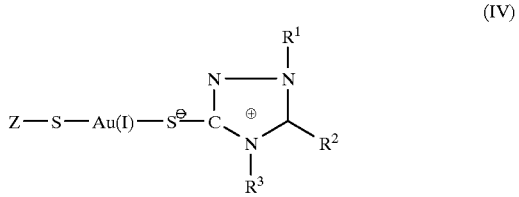   (IV)

wherein Z is as defined in claim 1, and $R^1$, $R^2$, and $R^3$ are independently hydrogen or an alkyl group having from 1 to 5 carbon atoms.

7. A photographic element according to claim 1 wherein the emulsion layer is a predominantly silver chloride emulsion layer.

8. A photographic element according to claim 6 wherein the emulsion layer is a predominantly silver chloride emulsion layer.

9. A photographic element according to claim 1 wherein Z is an alkyl group having from 1 to 8 carbon atoms, an aryl group having from 6 to 18 carbon atoms, or a heterocyclic group having from 5 to 12 carbon atoms and at least one oxygen, nitrogen or sulfur atom.

10. A photographic element according to claim 9 wherein Z is a heterocylic group having from 5 to 12 carbon atoms and at least one oxygen, nitrogen or sulfur atom.

11. A photographic element according to claim 1 wherein the emulsion layer contains from about 0.0001 to about 10 μmoles of the compound of formula (I) per mole of silver halide.

12. A photographic element according to claim 11 wherein the emulsion layer contains from about 0.001 to about 1 μmole of the compound of formula (I) per mole of silver halide.

13. A photographic element according to claim 12 wherein the emulsion layer contains from about 0.01 to about 0.1 μmole of the compound of formula (I) per mole of silver halide.

14. A photographic element according to claim 1 wherein the compound is

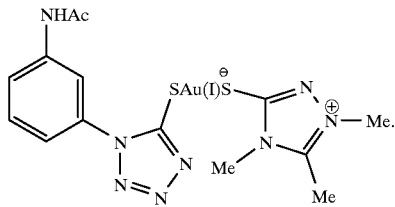

15. A photographic element comprising a support having situated thereon a silver halide emulsion layer, said emulsion layer having been chemically sensitized in the presence of a compound of the formula:

Z—S—Au(I)—S—Q  (I)

wherein

Z represents an alkyl, aryl, or heterocyclic group; and

Q represents a heterocyclic group wherein S and Q together represent a mesoionic group.

16. A photographic element according to claim 15 wherein the compound is of the formula:

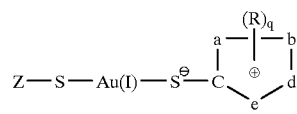  (III)

wherein

Z is as defined in claim 15;

a, b, d, and e represent atoms necessary to complete the heterocyclic group and are independently selected from carbon, nitrogen or chalcogen atoms, at least one of a, b, d, or e being nitrogen;

R is independently hydrogen or an alkyl, aryl, or heterocyclic group; and q is from 1 to 4.

17. A photographic element according to claim 16 wherein the compound is added to the emulsion layer before or during a heat treatment step of chemical sensitization in an amount from about 0.0001 to about 10 μmoles per mole of silver halide.

18. A compound of the formula:

Z—S—Au(I)—S—Q  (I)

wherein

Z represents an alkyl, aryl, or heterocyclic group; and

Q represents a heterocyclic group wherein S and Q together represent a mesoionic group.

19. A compound according to claim 18 wherein the compound is of the formula:

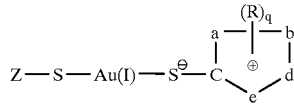  (III)

wherein

Z is as defined in claim 18;

a, b, d, and e represent atoms necessary to complete the heterocyclic group and are independently selected from carbon, nitrogen or chalcogen atoms, at least one of a, b, d, or e being nitrogen;

R is independently hydrogen or an alkyl, aryl, or heterocyclic group; and q is from 1 to 4.

20. A method of preparing a silver halide emulsion comprising precipitating silver halide grains in an aqueous colloidal medium to form an emulsion, heating the emulsion, and adding to the emulsion, either before or during heating, a Au(I) compound having the formula Z—S—Au(I)—S—Q  (I)

wherein

Z represents an alky, aryl, or heterocyclic group; and

Q represents a heterocyclic group wherein S and Q together represent a mesoionic group.

21. The method of claim 20 wherein wherein the compound is of the formula:

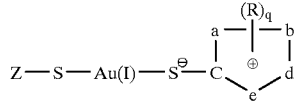  (III)

wherein

Z is as defined in claim 20;

a, b, d, and e represent atoms necessary to complete the heterocyclic group and are independently selected from carbon, nitrogen or chalcogen atoms, at least one of a, b, d, or e being nitrogen;

R is independently hydrogen or an alkyl, aryl, or heterocyclic group; and q is from 1 to 4.

22. The method of claim 20 wherein the silver halide emulsion is greater than 95 mole % silver chloride.

23. The method of claim 20 wherein the amount of the Au(I) compound added to the silver halide emulsion is from 0.1 μmol to 500 μmol per mole of silver.

24. The method of claim 20 wherein hypo is added to the emulsion either before or during heating.

* * * * *

UNITED STATES PATENT AND TRADEMARK OFFICE
CERTIFICATE OF CORRECTION

PATENT NO. : 5,912,112
DATED : June 15, 1999
INVENTOR(S) : Roger Lok, et al

It is certified that error appears in the above-identified patent and that said Letters Patent is hereby corrected as shown below:

Column 15, line 52, delete "Compound 22" and insert --Compound ZZ--.

Signed and Sealed this

Thirteenth Day of June, 2000

Attest:

Q. TODD DICKINSON

*Attesting Officer*        *Director of Patents and Trademarks*